(12) United States Patent
Anaebonam et al.

(10) Patent No.: US 6,254,891 B1
(45) Date of Patent: *Jul. 3, 2001

(54) EXTENDED RELEASE ACETAMINOPHEN

(75) Inventors: Aloysius O. Anaebonam, Burlington; Emmett Clemente, Manchester; Robert W. Mendes, Dedham, all of MA (US)

(73) Assignee: Ascent Pediatrics, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/146,261

(22) Filed: Sep. 3, 1998

(51) Int. Cl.$^7$ .............................. A61K 9/16; A61K 9/50
(52) U.S. Cl. .................... 424/497; 424/493; 424/494
(58) Field of Search ................... 424/497, 493, 424/494

(56) References Cited

U.S. PATENT DOCUMENTS

| | | | |
|---|---|---|---|
| 4,820,522 | 4/1989 | Radebaugh et al. | 424/468 |
| 4,867,984 | * 9/1989 | Patel . | |
| 4,874,613 | * 10/1989 | Hsiao . | |
| 4,952,402 | 8/1990 | Sparks et al. | 424/419 |
| 5,032,384 | 7/1991 | Yeh et al. | 424/49 |
| 5,773,031 | * 6/1998 | Shah et al. . | |
| 5,780,055 | * 7/1998 | Habib et al. . | |

OTHER PUBLICATIONS

*Remington's Pharmeceutical Sciences*, 18$^{th}$ ed., Mack Printing Company, Easton, PA (1990) pp. 592–593.

Oral Presentation, 98th Annual Meeting of the American Society for Clinical Pharmacol. and Therap., New Orleans, LA (Mar. 28, 1988).

S.C. Porter, "Coating of Pharmecutical Dosage Forms," *Remington's Pharmeceutical Sciences*, 18$^{th}$ ed., A.R. Gennaro ed., Chapter 90, Mack Publishing Co., Easton, PA (1990) pp. 1666–1675.

M.D. Rawlins, et. al., Eur. J. Clin. Pharmacol., 11:283–286 (1977). Pharmacokinetics of Paracetamol (Acetaminophen) after Intravenous and Oral Administration.

R. Langer, Science, 249:1527–1533 (1990). New Methods of Drug Delivery.

* cited by examiner

*Primary Examiner*—Diana Dudash
*Assistant Examiner*—Alysia Berman
(74) *Attorney, Agent, or Firm*—Welsh & Katz, Ltd.

(57) ABSTRACT

An extended release acetaminophen composition comprises particles containing acetaminophen coated on sugar/starch seeds. The particles are present as a blend of both an immediate release and a controlled release form. The composition, when contained within a gelatin capsule and assayed in a USP Apparatus I rotating basket at 50 rpm in 900 mL of phosphate buffer at pH 5.8 and a temperature of 37° C., exhibits about 40 percent acetaminophen dissolution at one-half hour, about 55 percent acetaminophen dissolution at one hour, and substantially complete dissolution of acetaminophen at six hours. A process for treating a human patient with the extended release acetaminophen composition is also disclosed.

2 Claims, 3 Drawing Sheets

EXTENDED RELEASE ACETAMINOPHEN

FIELD OF THE INVENTION

This invention relates to the extended release administration of medication. More particularly, the invention relates to an acetaminophen composition that has particular in vitro acetaminophen release characteristics and is adapted for use by human patients that have difficulty swallowing acetaminophen tablets, caplets or capsules.

BACKGROUND OF THE INVENTION

Coating medication to effect a controlled or extended release administration profile is well known in the art. Drug manufacturers have been using such methods to provide oral administration of medications that enter the body over a predetermined, extended period of time.

Controlled release administration provides many benefits to a patient. For example, controlled release administration can reduce the number of times that a patient is required to self-administer medication, thus reduce the possibility that the patient will forget to take his or her medication during the day Analgesics and antipyretics, such as acetaminophen are often self-administered over the course of a day to help alleviate pain or fever from which a person is suffering. Often, such symptoms can last for long periods of time. However, the symptoms need not affect the person's typical daily routine. Thus, the person may not remember to take his or her medication because of other daily activities.

As a result, it has become advantageous to provide an extended or controlled release analgesic drug for self-administration. Such controlled release administration can substantially reduce the number of times that a patient takes medication during the day. The controlled release properties also facilitate night time administration in that a controlled release coating can be provided to sufficiently extend over the period during which the person is asleep.

In preparing and applying a controlled or extended release coating it is known to prepare the medication in a quantity of small pellets, non-pareils or prills, which are small, generally spherically shaped form of the medication. The prills are coated with, for example, an aqueous, ethyl-cellulose based film coating product, which dissolves when subjected to humidity or liquid aqueous media. The prills can be contained within a gelatin capsule or blister. The capsule, like the ethyl-cellulose coating, dissolves when subjected to humid conditions or liquid aqueous media. The blister is typically not administered to a patient, but rather is opened or separated and the contents emptied therefrom for use.

One method of applying the coating to the prills utilizes a technique referred to in the art as panning. This technique was originally developed for sugar-coating and is discussed by S. C. Porter in "Coating of Pharmaceutical Dosage Forms", *Remington's Pharmaceutical Sciences,* 18th ed., A. R. Gennaro ed., Chapter 90, Mack Publishing Co., Easton Pa. (1990) pages 1666–1675.

U.S. Pat. No. 4,820,522 teaches the preparation of a sustained release acetaminophen preparation that includes hydroxyethyl cellulose as an excipient and povidone (polyvinyl pyrrolidone) as a granulating agent to form a shaped and compressed medicament. The resulting compressed medicament is provided in the form of a compressed tablet or as a layer of a multilayered tablet. In this composition, the povidone, hydroxyethyl cellulose and other ingredients bind the acetaminophen in a sustained release solid matrix. A composition of this patent is stated to further require the inclusion of a "wicking agent" such as microcrystalline cellulose to wick fluids into the matrix and also an "erosion promoter" such as pregelatinized starch. Although a composition of this patent provides sustained release of acetaminophen to normal adults, such a composition is tableted and as such, cannot provide the medication to a patient who has difficulty swallowing a tablet.

Accordingly, there continues to be a need for an extended release acetaminophen composition that can be used to treat children and adults who have difficulty swallowing tablets or capsules, and that exhibits a predictable profile for the extended release of the acetaminophen over a period of time.

SUMMARY OF THE INVENTION

The present invention contemplates an extended release composition of acetaminophen in the form of generally spherical particles. The particles can be administered in a gelatin capsule or blister, and the contents administered in the gelatin capsule to adults that can swallow such capsules or the contents of the capsule or blister can be emptied therefrom and dispersed in an edible medium such as applesauce that can be swallowed by patients such as children that cannot swallow or have difficulty swallowing tablets, caplets or capsules.

A contemplated extended release acetaminophen composition comprises a plurality of discrete particles containing acetaminophen coated on sugar/starch seeds. All of these particles are free of a wicking agent and an erosion promoter as required and utilized in U.S. Pat. No. 4,820,522. The particles are present as a blend of both an immediate release and a controlled release form. The composition, when present in a gelatin blister and assayed in a USP Apparatus I rotating basket at 50 rpm in 900 milliliters (mL) of phosphate buffer at pH 5.8 and 37° C., exhibits about 40 percent acetaminophen dissolution (released) at one-half hour, about 55 percent acetaminophen dissolution at one hour, and substantially complete dissolution of acetaminophen at six hours.

Advantageously, a contemplated extended release acetaminophen composition provides an extended or sustained release profile in a particle- or prill-containing gelatin capsule or blister. A contemplated composition can thus be dispersed or sprinkled on, for example, food such as applesauce, so that it can be administered to a patient that, otherwise has difficulty taking, or could not take a "solid" tablet or caplet. Thus, the present extended release composition now provides long term analgesic administration for patients who otherwise could not obtain such relief.

It is to be understood that reference herein to gelatin capsule, capsule or blister is made only for the purpose of describing or providing various alternate packaging or "containing" vehicles for the composition of the present invention, and is not intended to limit the scope of the present invention. All such packaging or "containing" vehicles are thus within the scope of the present invention.

In a preferred composition, the controlled release particles comprise a sugar/starch seed particle coated with a plurality of layers of acetaminophen and magnesium stearate that are bound with povidone. Most preferably, the acetaminophen-containing layers are coated with a plurality of layers of a mixture of povidone and magnesium stearate. In a contemplated composition, the weight ratio of acetaminophen to magnesium stearate in the controlled release particles is about 5:1 to about 10:1, and acetaminophen comprises about 70 to about 80 weight percent of the controlled release particles.

Preferably, the immediate release particles also comprise sugar/starch seed particles, which seeds are coated with a plurality of layers of a mixture of acetaminophen, starch and cross-linked carboxymethyl cellulose bound with povidone. A preferred cross-linked carboxymethyl cellulose is croscarmellose NF. In a preferred composition, the immediate release particles contain acetaminophen, starch and cross-linked carboxymethyl cellulose in a weight ratio of about 13–16:1:1.5–2, respectively, and acetaminophen constitutes about 60–70 weight percent of the particles.

A preferred blend of the composition includes immediate release particles and controlled release particles in a weight ratio of about 1:1 to about 1:1.5, respectively.

The blend can also contain coated sugar/starch seeds that are free of acetaminophen. In one such blend, the immediate release particles, the controlled release particles and the coated sugar/starch seeds are present in a weight ratio of about 1:1–1.5:0.1–0.25.

A process for treating a human patient that has difficulty swallowing acetaminophen in tablet, caplet or capsule form includes the steps of distributing an effective amount of the particles in a pharmaceutically acceptable palatable medium to form an acetaminophen particle-containing medium and administering the acetaminophen particle-containing medium to the human patient.

The present process is particularly contemplated for administering the composition to human patients that are about three months to about 14 years old, and particularly to children 2 to about 11 years old, including children that are febrile. However, the composition can be used by others that may have difficulty swallowing a tablet, caplet or capsule, or it can be used by those that do not have difficulty taking such "solid" non-dispersible medication forms.

Other features and advantages of the present invention will be apparent from the following detailed description, the accompanying drawings, and the appended claims.

BRIEF DESCRIPTION OF THE FIGURES

In the figures forming a portion of this disclosure.

DETAILED DESCRIPTION OF THE PREFERRED EMBODIMENTS

Figure 1:
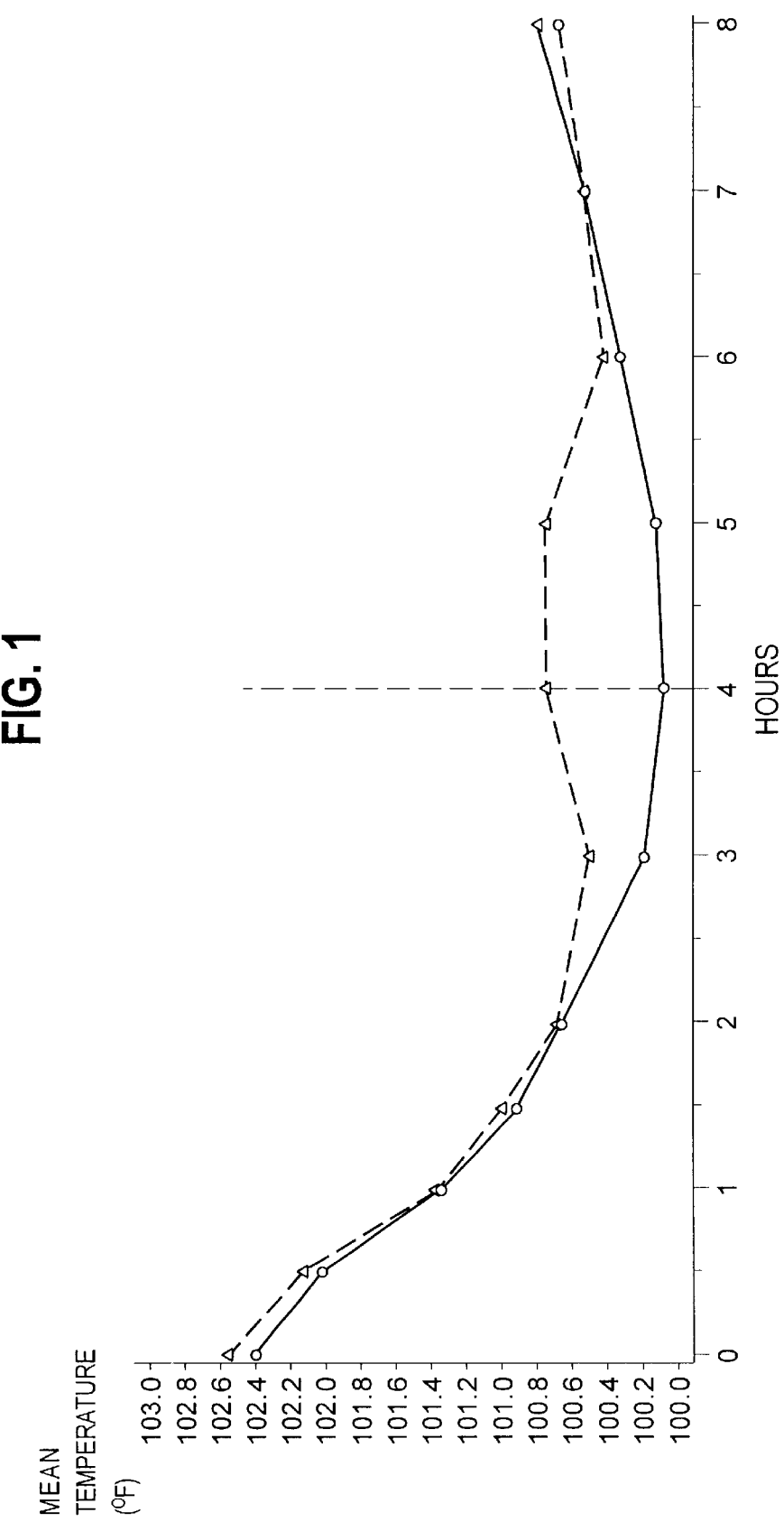
FIG. 1 is graphic illustration of the overall results of a randomized trial comparing the present acetaminophen composition and Children's Tylenol® Immediate Release Elixir in febrile children, showing the mean temperature in degrees Fahrenheit as a function of time, in which the circles represent data for a contemplated acetaminophen composition and the triangles represent data for the Tylenol® Immediate Release Elixir product.

The present invention contemplates extended release acetaminophen. The acetaminophen is present as a composition of a blend of beads or particles (also referred to herein as pellets, prills or non-pareils) of both an immediate release form and a controlled or sustained release form. The composition, when contained within a gelatin capsule and assayed in vitro using the USP Apparatus I rotating basket protocol in 900 mL of phosphate buffer at a pH value of about 5.8 and at a temperature of about 37° C., exhibits about 40 percent acetaminophen dissolution (release) after about one-half hour, about 55 percent dissolution after about one hour, and substantially complete dissolution after about six hours. Exemplary data for dissolution and contemplated compositions are illustrated hereinafter.

A composition prepared in accordance with the present invention exhibits surprising and significant advantages over known acetaminophen preparations. Specifically, the composition exhibits substantial temperature depression in febrile children, and particularly at time periods after about 2½ hours after administration, compared to equally administered amounts of known immediate release acetaminophen preparations.

More surprisingly, an extended release acetaminophen composition prepared in accordance with the present invention exhibited sustained temperature depression compared to the known, commercial acetaminophen preparation, at a time period between about 4 hours and 6 hours, even after subsequent administration of the commercial preparation at 4 hours after initial administration.

As will be recognized by those skilled in the art, the sustained temperature depression, i.e., fever relief, has extreme benefits when administered to small children. Medical professionals, as well as parents and caregivers of small children know well that it is difficult if not impossible to have a small child swallow a pill or tablet. As such, it was previously unknown to provide an extended release acetaminophen composition to a child.

The present extended release acetaminophen composition provides such long term relief in a palatable form. The present composition permits administration of the medication to a child so that the child can benefit from the extended release formulation. This single dose administration can be extremely beneficial at night, when it may now be possible for a child to rest or sleep comfortably for a sufficiently long period of time, eight or more hours, while under the effects of the analgesic, as compared to having to wake the child to provide a second administration. Parents know all too well that a "good night's rest" can be beneficial to the comfort and recovery of an ill child.

A. The Composition

The composition includes particles containing acetaminophen coated on sugar/starch seeds. The particles are a blend of particles having an immediate release form and particles having a controlled release form. A preferred composition further includes inactive particles or nonpareils (also referred to herein as placebo beads), such as coated sugar/starch seeds. An anticipated composition is contained within a blister (or a gelatin capsule that can be orally administered as a capsule), that can be opened and the particles mixed with, for example, food such as applesauce, tapioca, flavored pudding or yogurt for those patients that have difficulty or cannot swallow a capsule, tablet or caplet.

Dissolution profiles or specifications have been developed for the present acetaminophen preparation based upon two accepted assaying techniques, namely the rotating basket and rotating bottle methods, which are discussed in detail below. The specifications include particularly preferred dissolution values based upon regulatory, i.e., FDA, requirements and "in-house" requirements as determined by the rotating basket method and "in-house" requirements as determined by the rotating bottle method.

Preferred dissolution profiles are as shown in Tables 1 and 2 below.

TABLE 1

DISSOLUTION PROFILES FOR
THE PRESENT EXTENDED RELEASE
ACETAMINOPHEN PREPARATION AS MEASURED
BY THE ROTATING BASKET METHOD

| Time (minutes) | Percent Dissolved (range) |
|---|---|
| 15 | 41 (33–49) |
| 30 | 47 (38–56) |
| 60 | 53 (43–64) |
| 120 | 65 (52–78) |
| 180 | 74 (59–89) |
| 240 | 82 (66–98) |
| 300 | NLT 90 |

TABLE 2

DISSOLUTION PROFILES FOR
THE PRESENT EXTENDED RELEASE
ACETAMINOPHEN PREPARATION AS MEASURED BY
THE ROTATING BOTTLE METHOD

| Time (minutes) | Percent Release (range) |
|---|---|
| 15 | 50 (45–55) |
| 60 | 60 (54–66) |
| 120 | 70 (63–77) |
| 180 | 80 (72–88) |
| 240 | >90 |

Several of the dissolution value ranges presented above overlap such that an upper limit of a range at a particular time can have a higher percent dissolved than a lower limit of a range at a next later time. This is not to imply that the dissolution value is constant or reverses as time progresses. Rather, dissolution follows a substantially smooth curve with the total amount of acetaminophen being dissolved increasing over time until substantially all of the acetaminophen is dissolved.

As discussed herein, the final distribution of immediate release particles, controlled release particles and placebo particles is made to effect these dissolution profiles provided in Tables 1 and 2. These assay techniques are discussed hereinafter.

The extended release acetaminophen composition is a blend of an immediate release form and a controlled or sustained release form that contains acetaminophen coated on sugar/starch seeds. A preferred composition further includes inactive, acetaminophen-free particles or nonpareils (also referred to herein as placebo beads or particles), such as sugar coated starch seeds.

The extended release acetaminophen composition includes a distribution of controlled release particles and immediate release particles that is made to effect a desired dissolution profile, that is dependent upon results of in-process testing. The batch amounts of the particles that are used to prepare the distribution are about 110 kg to about 140 kg of controlled release particles, about 90 kg to about 115 kg of immediate release particles and about zero kg to about 50 kg of placebo particles. Those skilled in the art will recognize that the weights of the various particles in each dosage; e.g., blister or capsule, can be varied depending upon the particular dosage desired, however, the weights of the immediate release and controlled release particles relative to one another typically remain relatively constant, to achieve that desired distribution and thus the desired dissolution profile.

It will also be recognized by those skilled in the art that the particular "dosage" provided in a given blister or capsule can vary depending upon the desired dosage. Anticipated desired dosages are 160 mg, 240 mg, 325 mg and 650 mg blisters.

The controlled release particles include acetaminophen, magnesium stearate and povidone disposed on a sugar/starch seed or core. A preferred sugar/starch seed is sugar spheres NF of between about 40 and 50 mesh, that contain not less than 62.5 percent and not more than 91.5 percent sucrose, calculated on the dry basis, the remainder consisting primarily of starch. (USP NF 1995 2313).

In a preferred form, the controlled release particles include a plurality of layers of acetaminophen and magnesium stearate on the sugar/starch seeds, which layers are bound with povidone. Most preferably, the acetaminophen-containing layers are coated with a plurality of layers of a mixture of povidone and magnesium stearate.

One preferred preparation of the controlled release particles includes acetaminophen in a weight ratio to magnesium stearate of about 5:1 to about 10:1, and the acetaminophen is about 70 to about 80 weight percent of the controlled release particles.

A contemplated batch formula for the controlled release particles includes "Starter Beads" having a batch formula of about 100 kg of acetaminophen, about 5.3 kg of magnesium stearate NF, about 21.6 kg of sugar spheres NF (40 to 50 mesh), about 17 kg to about 30 kg of 15 percent povidone/isopropyl alcohol (IPA) stock solution, and about 47 kg to about 80 kg of isopropanol.

A 130.2 kg batch of the "Starter Beads" that is used to prepare the controlled release particles then has added thereto as additional coatings, about 5.85 kg to about 15.6 kg of magnesium stearate NF, about 2.4 L to about 6.4 L of isopropanol and about 2.4 L to about 6.4 L of 15 percent povidone/IPA stock solution. The amount (i.e., weight) of magnesium stearate, isopropanol and povidone/IPA solution applied as the coating are dependent upon the number of coatings required to meet specifications; i.e., the desired dissolution profile, as determined during in-process assays.

The immediate release particles are likewise formed of sugar/starch seeds having a plurality of layers of a mixture of acetaminophen, starch and a cross-linked carboxymethyl cellulose, preferably, croscarmellose sodium NF, that is bound with povidone. Preferably, the acetaminophen is present in a weight ratio to the starch and to the carboxymethyl cellulose of about 13–16:1:1.5–2, respectively, and the acetaminophen is about 60–70 weight percent of the immediate release particle.

A contemplated batch formula for the immediate release beads includes about 100 kg of acetaminophen, about 7.1 kg of cross-linked carboxymethyl cellulose, preferably croscarmellose NF, about 11.9 kg of starch NF, about 25.6 kg of sugar spheres NF (40 to 50 mesh) about 19 kg to about 34 kg of 15 percent povidone/IPA stock solution, and about 53 kg to about 91 kg of isopropanol.

The composition can further include, as part of the blend, placebo particles of coated sugar/starch seeds that do not contain acetaminophen. Preferably, the coated sugar spheres have a size of between about 30 and about 35 mesh.

A contemplated batch formula for the placebo particles includes about 10 kg of ethylcellulose 7-FP, about 50 kg of sugar spheres NF (30–35 mesh), about 1.2 kg of methylcellulose E-5, and purified water as needed.

A final distribution of immediate release particles, controlled release particles and placebo particles is made to effect a predetermined dissolution profile, and can be made to effect the particularly preferred dissolution profiles provided in Tables 1 and 2. The assay techniques are discussed hereinafter.

B. Composition Preparation

The various particles that form the composition; i.e., the immediate release particles, the controlled release particles and the placebo particles are each prepared in separate processes as presented below, and are subsequently blended together to form the present extended release acetaminophen composition.

i. Immediate Release Particle Preparation

The immediate release particles are prepared in two batches. A 100 kilogram (kg) quantity of acetaminophen, a 7.1 kg quantity of croscarmellose sodium NF, and an 11.9 kg quantity of starch NF, are each divided in half, and the three constituents are blended together to form two identical batches.

Each of the batches is milled through an 80 mesh screen using a mill such as a Fitzpatrick Mill. The two milled batches are then blended together to form a mixture, which is tested for composition in accordance with accepted quality assurance testing methods that are well-known by those skilled in the art.

The acetaminophen mixture is subsequently divided into three equal parts, with a first part remaining whole, and second and third parts each divided into lots of 50 percent, 30 percent and 20 percent.

A 25.6 kg quantity of 40–50 mesh sugar/starch seeds; e.g., sugar spheres NF, is placed in a stainless steel coating pan. An 80 liter (L) quantity of 5 percent povidone/IPA solution is prepared for spraying onto the particles.

The coating pan is started with the sugar spheres, onto which is sprayed an application (approximately 0.173 kg per application) of the povidone-alcohol solution, and onto which is sifted an application (approximately 0.32 kg) of the acetaminophen mixture from the first part (that part that remained whole). Sifting is done using a standard sifter. The spraying and sifting steps are continued until the first part of the mixture has been applied to the sugar spheres to form a batch of partially coated spheres.

The partially coated spheres are then divided into two equal lots, each lot being placed in a coating pan. Separately for each of the two lots, spraying of the povidone/IPA solution and sifting of the acetaminophen mixture as divided into the 50 percent lots continues until the 50 percent lots have been applied to the spheres. Following application of the 50 percent lots, the spheres can be screened using a 25 mesh screen if necessary.

The spraying of the povidone/IPA solution and sifting of the acetaminophen mixture as divided into the 30 percent lots commences and continues until the 30 percent lots have been applied to the spheres. The coated spheres can be rescreened using a 25 mesh screen.

Spraying of the povidone/IPA solution and sifting of the acetaminophen mixture continues using the mixture as divided into the 20 percent lots until the 20 percent lots have been applied to the spheres. At this point in the process, the entire quantity of the acetaminophen mixture has been applied to the spheres, and about 50 kg of the 5 percent povidone/IPA solution has been applied to the spheres.

A 7.5 percent povidone/IPA solution is prepared and applied to the spheres as a sealant. The sealed spheres are tumble dried for about one hour, weighed, and placed in an oven at about 122° F. for 24 hours. After drying, the spheres are screened through a 20 mesh screen and a 38 mesh screen to form the immediate release particles.

Those skilled in the art will recognize that the various mixtures and solutions are to be weighed, tested and assayed at selected stages during the process. Those skilled in the art will also recognize that the isopropanol as well as the isopropyl alcohol component of the povidone/IPA solution evaporate during the production process, and as such, their weights are not considered in the total particle weight of the final immediate release particles.

ii. Controlled Release Particle Preparation

The controlled release particles are prepared in a similar process to that used for preparing the immediate release particles, employing a repeated spray and sift process.

"Starter Beads" are first prepared using a 100 kg quantity of acetaminophen and a 5.3 kg quantity of magnesium stearate that are each divided in half, and the two constituents blended together to form two identical batches. Each of the batches is milled through an 80 mesh screen using a mill such as a Fitzpatrick Mill. The two milled batches are then blended together to form one mixture, which is tested for composition in accordance with accepted quality assurance assaying methods.

The acetaminophen mixture is subsequently divided into three equal parts, with a first part remaining whole, and second and third parts each divided into lots of 50 percent, 30 percent and 20 percent.

A 21.6 kg quantity of 40–50 mesh sugar/starch seeds, such as sugar spheres NF, is placed in a stainless steel coating pan. An 80 liter (L) quantity of 5 percent povidone/IPA solution is prepared for spraying onto the particles.

The coating pan is started with the sugar spheres, onto which is sprayed an application (approximately 0.16 kg per application) of the povidone/IPA solution, and onto which is sifted an application (approximately 0.3 kg) of the acetaminophen mixture from the first part (that part that remained whole). Sifting is done using a standard sifter. The spraying and sifting steps continue until the first part of the mixture has been applied to the sugar spheres to form a batch of partially coated spheres.

The partially coated spheres are then divided into two equal lots, each lot being placed in a coating pan. Separately for each of the two lots, spraying of the povidone/IPA solution and sifting of the acetaminophen mixture divided into 50 percent lots continues until the 50 percent lots have been applied to the spheres. Following application of the 50 percent lots, the spheres can be screened using a 25 mesh screen if necessary.

Spraying of the povidone/IPA solution and sifting of the acetaminophen mixture as divided into the 30 percent lots commences and continues until the 30 percent lots have been applied to the spheres. The coated spheres can be rescreened through a 25 mesh screen if necessary.

The spraying of the povidone/IPA solution and sifting of the acetaminophen mixture commences and continues using the mixture divided into 20 percent lots until the 20 percent lots have been applied to the spheres. At this point in the process, the entire quantity of the acetaminophen mixture has been applied to the spheres, and about 50 kg of the 5 percent povidone/IPA solution has been applied to the spheres.

A 7.5 percent povidone/IPA solution is prepared and applied to the spheres as a sealant. Sealed spheres are tumble-dried for one hour, weighed, and placed in an oven at about 122° F. for 24 hours. After drying, the spheres are screened using a 20 mesh screen and a 38 mesh screen, which screened beads form the "Starter Beads."

An additional 7.5 percent povidone/IPA solution is prepared, and the "Starter Beads" are divided into two equal panloads. A quantity of magnesium stearate necessary to coat the particle is then prepared.

The beads are wetted by applying a quantity (approximately 0.7 L) of the povidone/IPA solution and are coated by applying about 0.8 kg of magnesium stearate. The coated "Starter Beads" are dried for about 15 minutes.

The steps of wetting with povidone/IPA solution and coating with magnesium stearate continue until a desired number of "coats" has been achieved. The coated beads are assayed and a release pattern is obtained during in-process testing. The "coating" can then be repeated until a desired release pattern is achieved, that is, until the beads are within specifications.

After coating is complete, the beads are placed in an oven and dried at ambient temperature for about 16 to about 24 hours. The beads, which are now the controlled release particles, are sampled, tested and screened using a 20 mesh screen.

iii. Placebo Particle Preparation

The placebo particles are also prepared in a "spray and sift" process, similar to the controlled and immediate release particles. Two 2.5 kg quantities and one 5 kg quantity of ethylcellulose (Ethocel® 7-FP) are dispensed. A 1.2 kg quantity of methylcellulose (Methocel® E-5) and 50 kg of 30–35 mesh sugar/starch seeds, such as sugar spheres NF are also dispensed.

The methylcellulose is prepared as a coating suspension in accordance with manufacturers instructions and is left to stand for at least 8 hours prior to use.

The sugar spheres are placed in a stainless steel coating pan, the pan is started, and the spheres are wetted with the methylcellulose suspension (approximately 0.211 kg per application) using a pressurized gun. Ethylcellulose powder (approximately 0.37 kg per application) is then sifted onto the wetted spheres using a standard sifter.

The wetting and sifting steps are continued until the first (5 kg) portion of ethylcellulose is applied. The spheres are then screened using a 24 mesh screen and the wetting and sifting steps continued until the spheres reach 24 mesh on a 30 mesh screen.

The spheres are tumbled in the coating pan, weighed and assayed in accordance with accepted quality assurance assay methods that are well-known by those skilled in the art. Subsequent to assaying, the spheres are placed in an oven and dried at about 122° F. for at least 24 hours. After drying, the spheres (now placebo particles or beads) are screened using 20 mesh and 30 mesh screens.

Physio-Chemical and Efficacy Studies

Physio-chemical and efficacy studies were conducted in order to determine the dissolution rates and to determine the effectiveness of the extended release composition. The physio-chemical studies were conducted in vitro and included rotating basket assays. Once suitable in vitro rates for these dissolutions were in hand, dissolution of a contemplated extended release acetaminophen composition prepared in accordance with the present invention was then compared to a known, commercially available acetaminophen product, namely Tylenol® Extended Relief Caplets (in 650 mg dose), as an external standard.

Efficacy studies were conducted in vivo to determine the comparative effectiveness for producing long term temperature depression or relief of the present acetaminophen composition relative to a known commercially available acetaminophen product, namely Children's Tylenol® Immediate Release Elixir.

a. In Vitro Dissolution Studies

The dissolution studies included comparative studies of the dissolution rates of the acetaminophen composition of the present invention to the dissolution rates of Tylenol® Extended Relief Caplets (650 mg). The studies included rotating basket tests that were carried out in accordance with accepted methods as provided in USP 23/NF 18, United States Pharmacopeial Convention, Inc., Rockville, Md. 1791 (1994).

Rotating Basket Assays

The rotating basket assays were carried out in accordance with USP 23/NF 18 accepted procedure. The testing apparatus for each of the samples; i.e., Tylenol® Extended Relief Caplets and the acetaminophen composition of the present invention was a USP Apparatus I, rotating at 50 rpm, using a medium of 900 mL of phosphate buffer at a pH of 5.8 and at a temperature of 37° C. Six samples of each lot of the products (i.e.; the Tylenol® Extended Relief Caplet product and a contemplated acetaminophen composition) were assayed at times of 10, 20, 30, 45, 60, 120, 360, 480 and in some cases 720 minutes. Filters used were Hanson Probe 10 $\mu$m.

The test medium was analyzed for UV absorbance of the test solution vs. standard acetaminophen (APAP), USP at 244 nm. The samples (indicated as Smpl in the following Tables 3–6) assayed included a contemplated acetaminophen composition in one dosage of 650 mg (Table 3), and two sets of samples of the Tylenol® Extended Relief Caplet product (Lot #MFM437 and Lot #PEM910, in Tables 4 and 5, respectively). The results of the of the rotating basket assays are shown below in Tables 3, 4 and 5. The comparison of the results of one of the Tylenol® Extended Relief Caplet lots of samples and the present acetaminophen preparation are summarized in Table 6, below.

TABLE 3

PERCENT DISSOLUTION OF
THE PRESENT CONTROLLED RELEASE
ACETAMINOPHEN COMPOSITION
(650 mg, Lot # EXPT 9236)

| Time (Min.) | Smpl 1 | Smpl 2 | Smpl 3 | Smpl 4 | Smpl 5 | Smpl 6 | Mean |
|---|---|---|---|---|---|---|---|
| 10 | 13.6 | 10.7 | 11.5 | 11.4 | 15.1 | 13.6 | 12.6 |
| 20 | 27.5 | 33.6 | 28.9 | 26.5 | 30.3 | 26.7 | 28.9 |
| 30 | 37.9 | 40.6 | 36.9 | 38.1 | 39.0 | 36.7 | 38.2 |
| 45 | 48.3 | 50.7 | 46.9 | 45.7 | 48.9 | 48.1 | 48.1 |
| 60 | 57.0 | 59.5 | 55.1 | 54.0 | 58.7 | 56.7 | 56.8 |
| 120 | 83.0 | 83.8 | 79.2 | 78.5 | 82.6 | 82.9 | 81.7 |
| 360 | 101.1 | 100.9 | 98.4 | 97.8 | 100.0 | 101.3 | 99.9 |
| 480 | 104.7 | 105.8 | 102.4 | 102.5 | 102.3 | 103.8 | 103.6 |
| 720 | 103.7 | 104.5 | 104.7 | 102.8 | 104.1 | 106.2 | 104.2 |

TABLE 4

PERCENT DISSOLUTION OF
TYLENOL ® EXTENDED RELIEF CAPLET
(1 CAPLET @ 650 mg., Lot # MFM437)

| Time (Min.) | Smpl 1 | Smpl 2 | Smpl 3 | Smpl 4 | Smpl 5 | Smpl 6 | Mean |
|---|---|---|---|---|---|---|---|
| 10 | 29.9 | 33.4 | 41.6 | 39.7 | 42.0 | 41.8 | 38.1 |
| 20 | 48.5 | 49.0 | 51.1 | 50.6 | 49.8 | 51.0 | 50.0 |
| 30 | 53.3 | 56.3 | 54.0 | 51.2 | 53.5 | 56.7 | 54.2 |
| 45 | 58.5 | 57.2 | 62.9 | 57.2 | 59.7 | 62.9 | 59.7 |
| 60 | 63.6 | 60.5 | 68.0 | 63.1 | 64.2 | 67.2 | 64.4 |
| 120 | 73.7 | 75.6 | 74.4 | 80.1 | 74.0 | 74.1 | 75.3 |
| 360 | 102.5 | 100.5 | 100.9 | 102.1 | 101.6 | 99.1 | 101.1 |

TABLE 4-continued

PERCENT DISSOLUTION OF
TYLENOL ® EXTENDED RELIEF CAPLET
(1 CAPLET @ 650 mg., Lot # MFM437)

| Time (Min.) | Smpl 1 | Smpl 2 | Smpl 3 | Smpl 4 | Smpl 5 | Smpl 6 | Mean |
|---|---|---|---|---|---|---|---|
| 480 | 102.8 | 100.8 | 98.7 | 99.9 | 100.7 | 100.2 | 100.5 |
| 720 | 103.2 | 101.4 | 105.4 | 102.3 | 103.5 | 102.5 | 103.1 |

TABLE 5

PERCENT DISSOLUTION OF
TYLENOL ® EXTENDED RELIEF CAPLET
(1 CAPLET @ 650 mg., Lot # PEM 910)

| Time (Min.) | Smpl 1 | Smpl 2 | Smpl 3 | Smpl 4 | Smpl 5 | Smpl 6 | Mean |
|---|---|---|---|---|---|---|---|
| 10 | 44.0 | 45.4 | 44.1 | 47.9 | 49.0 | 46.6 | 46.1 |
| 20 | 51.8 | 50.7 | 53.3 | 53.3 | 52.6 | 53.8 | 52.6 |
| 30 | 58.2 | 57.9 | 56.2 | 57.0 | 59.3 | 59.4 | 58.0 |
| 45 | 61.9 | 63.1 | 60.8 | 60.9 | 62.3 | 63.2 | 62.0 |
| 60 | 64.8 | 65.5 | 65.0 | 64.0 | 65.4 | 66.2 | 65.1 |
| 120 | 79.5 | 79.5 | 77.7 | 76.9 | 79.8 | 78.2 | 78.6 |
| 360 | 103.2 | 104.3 | 99.6 | 103.1 | 100.1 | 102.1 | 102.1 |
| 480 | 104.8 | 102.7 | 101.9 | 103.1 | 101.5 | 100.9 | 102.5 |

TABLE 6

CONDENSED SUMMARY OF RESULTS OF ROTATING BASKET
DISSOLUTION COMPARISON OF THE PRESENT
CONTROLLED RELEASE ACETAMINOPHEN (Lot # EXPT9236)
and TYLENOL ® EXTENDED RELIEF
CAPLETS (Lot # PEM910)

| Time (min.) | Acetaminophen (percent dissolved) | Tylenol ® (percent dissolved) |
|---|---|---|
| 10 | 12.6 | 46.1 |
| 20 | 28.9 | 52.6 |
| 30 | 38.2 | 58.0 |
| 45 | 48.1 | 62.0 |
| 60 | 56.8 | 65.1 |
| 120 | 81.7 | 78.6 |
| 360 | 99.9 | 102.1 |
| 480 | 103.6 | 102.5 |

As can be seen from the data of Tables 3–6, a contemplated acetaminophen preparation exhibited a more controlled and slower sustained release, particularly at early time periods, than did the Tylenol® Extended Relief Caplet product. At some time between 10 and 20 minutes after commencement of the test, over 50 percent of the Tylenol® Extended Relief Caplet product had dissolved. After one hour almost two-thirds of the Tylenol® Extended Relief Caplet product had dissolved, and almost 80 percent by two hours.

In contrast, a contemplated acetaminophen preparation had achieved about 40 percent dissolution at one-half hour, about 50 percent dissolution between 45 minutes and one hour, about 55 percent dissolution at one hour and after two hours had reached about an 82 percent dissolution. At six hours, a contemplated extended release acetaminophen composition exhibited complete dissolution. Thus, it can be seen from the data that the present acetaminophen preparation showed greater sustainability, particularly in the short term.

Those in vitro dissolution rates were measured in vitro in 900 mL of phosphate buffer at pH 5.8 and at a temperature of 37° C. in a USP Apparatus I rotating basket at 50 rpm.

Surprisingly, the in vitro dissolution rate of a contemplated sustained release composition is substantially the same as that observed for the in vitro sorption rate for the same composition.

Rotating Bottle Assay Techniques

Rotating bottle assays were carried out in order to establish dissolution profiles, such as the particularly preferred dissolution profile as illustrated in Table 2, for the contemplated acetaminophen composition. The rotating bottle assays were carried out in accordance with a variant of NF XIV, American Pharmaceutical Association, Washington, D.C. 985 (1974), procedure. The assay apparatus was a rotating bottle apparatus, rotating at 30 rpm, using a medium of 60 mL of modified gastric fluid prepared in accordance with the aforenoted NF XIV. The assay methods varied from the accepted NF XIV procedure in that the pH of the fluid used (gastric fluid) differed from that of the NF XIV procedure, and the duration of the assay that was carried out (one hour) differed from that of the NF XIV procedure.

In Vivo Studies

Randomized trial studies were conducted to determine whether a contemplated acetaminophen composition administered as a single dose for an 8 hour period was as efficacious in reducing fever as Children's Tylenol® Immediate Release Elixir, administered in two doses, in febrile children between the ages of 2 and 11 having initial temperatures $\geq 101.0°$ F. Administration was carried out using a contemplated acetaminophen composition at an initial administration time and a placebo at four hours post initial administration, and the Tylenol® Immediate Release Elixir product at initial administration and at four hours post initial administration. It is noted that the Tylenol® Immediate Release Elixir product labeling states that four hours should elapse between administrations.

The study group included 120 children; 59 received the Tylenol® Immediate Release Elixir product and 61 received a contemplated acetaminophen composition. Some of the children were also treated, concomitantly, with antibiotics.

Temperature measurements were recorded at pre-dose, ½, 1, 1½, 2, 3, 4, 5, 6, 7 and 8 hours after initial administration. Temperatures were measured using an Exergen LighTouch Infrared Ear Thermometer, which uses an arterial heat balance method.

Figure 2:
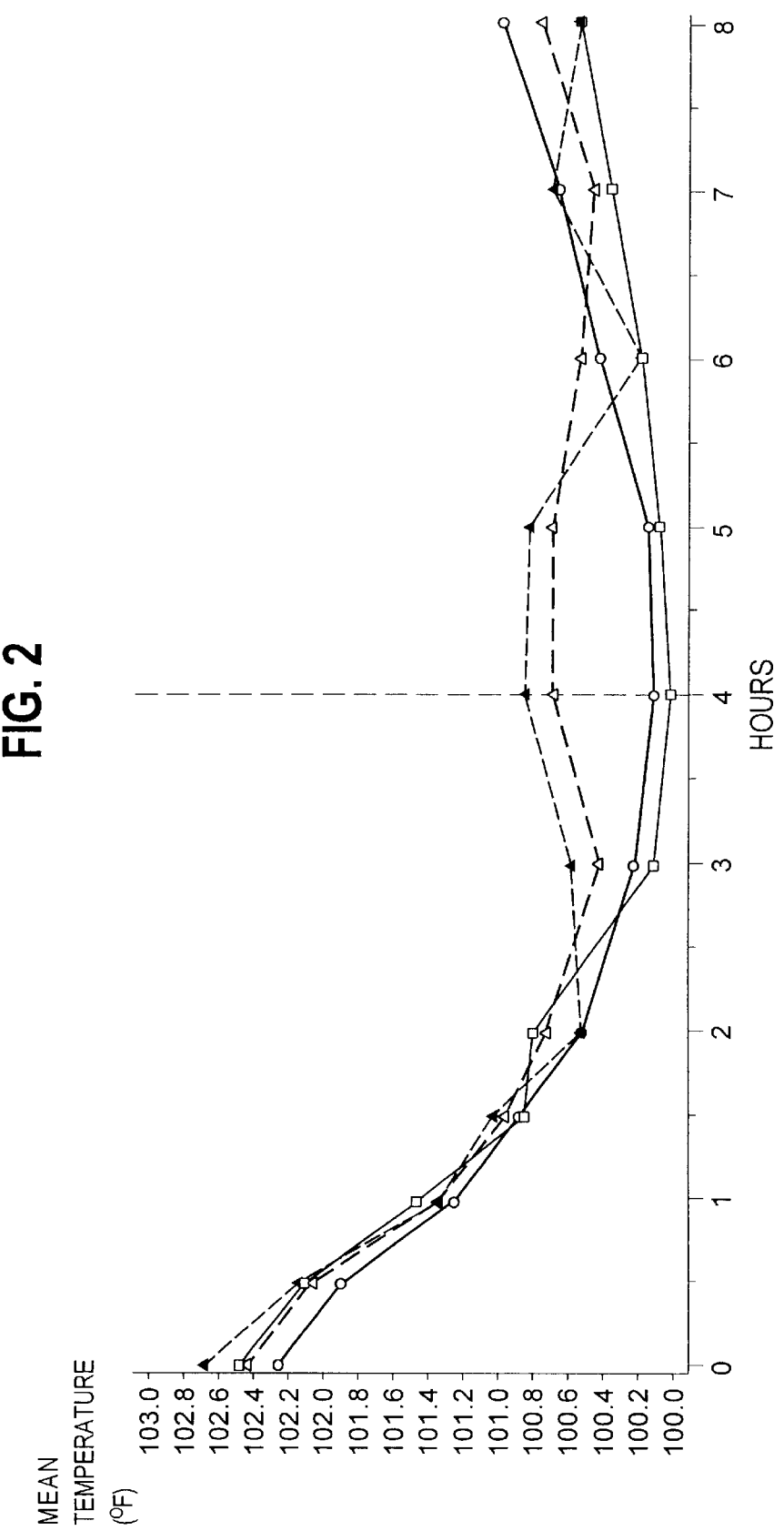
FIG. 2 is a graphic illustration of the data of FIG. 1 in which the data are segregated by the concomitant use and nonuse of an antibiotic. Here, the filled and empty circles represent data for a contemplated acetaminophen composition with and without, respectively, the concomitant use of an antibiotic, whereas the filled and empty triangles represent data for the Tylenol® Immediate Release Elixir product with and without, respectively, the concomitant use of an antibiotic.
Figure 3:
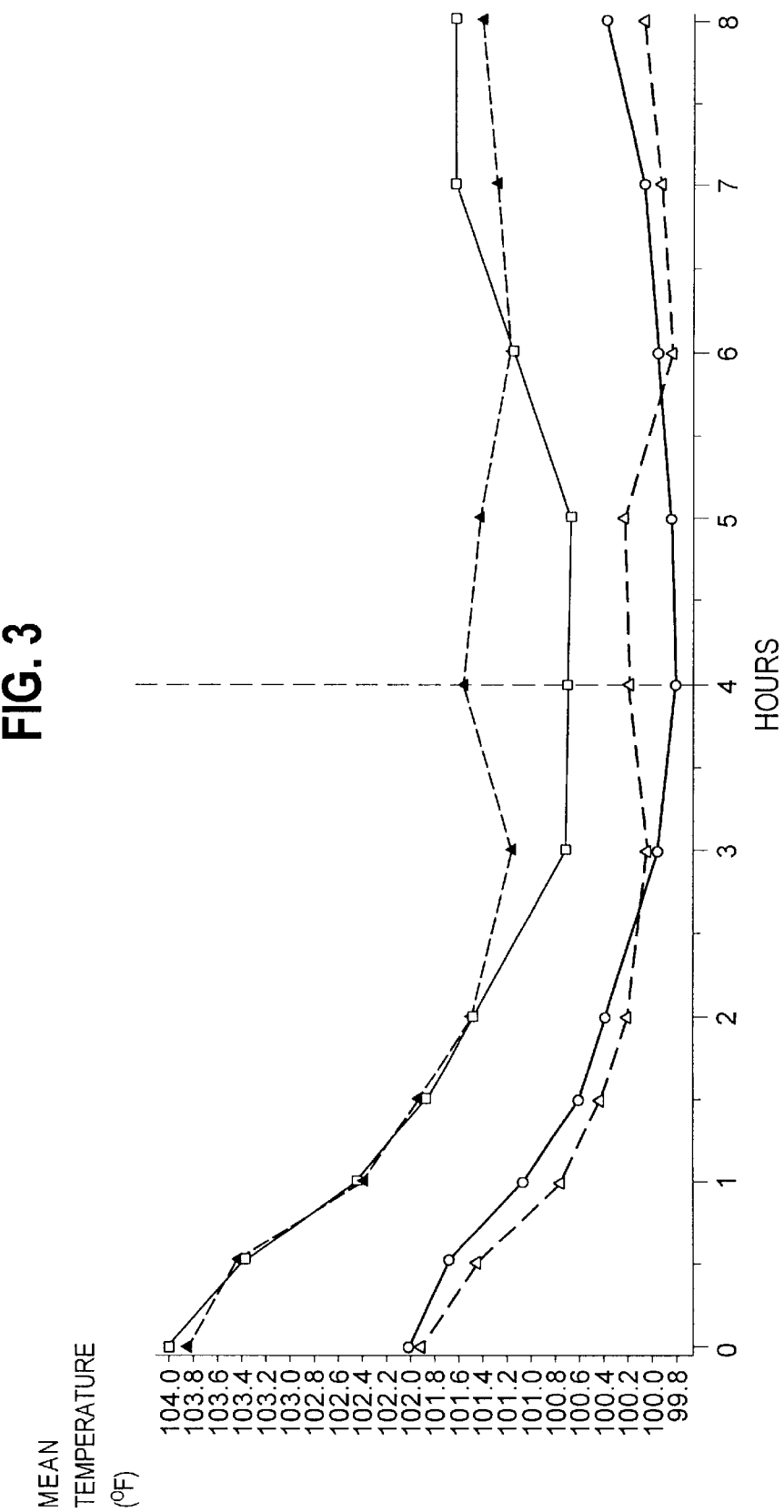
FIG. 3 is a graphic illustration of the data of FIG. 1 in which the data are segregated by high and low baseline temperatures. In this figure, the filled and empty circles represent data for a contemplated acetaminophen composition at high and low baseline temperatures, respectively, and the filled and empty triangles represent data for the Tylenol® Immediate Release Elixir product at high and low baseline temperatures, respectively.

The results of the studies are shown in FIGS. 1–3. In all of the figures, the circles (filled and empty) represent the data for a contemplated acetaminophen composition (preparation) and the triangles (filled and empty) represent the data for the Tylenol® Immediate Release Elixir product. FIG. 1 shows the overall results in mean temperature as a function of time, and includes all of the results, including children with both moderate and severe initial fevers (low and high baseline temperatures, respectively), as well as children that were concomitantly administered antibiotics. FIG. 2 shows the mean temperature over time and is segregated by antibiotic use. FIG. 3 shows the mean temperature over time and is segregated by high and low baseline temperatures.

As can be seen from the results, in every case, the effect of the Tylenol® Immediate Release Elixir product began to decrease after about two hours, as indicated by the decline in temperature reduction rate after two hours and an increase in temperature levels after about three hours.

Significantly, even after re-administration at four hours after initial administration (shown by the dotted vertical line at 4 hours), the temperature-reducing effect of the Tylenol® Immediate Release Elixir product required about two hours until it achieved an effect that approached the same or an equivalent effect to that of a contemplated acetaminophen composition. That is, a contemplated acetaminophen composition exhibited a significantly greater ability to reduce and maintain reduced temperatures in a single dosage than an equivalent amount of the Tylenol® Immediate Release Elixir product. This result was quite unexpected because the bioavailability of both materials was equivalent.

Referring to FIG. 2, wherein the filled circles and triangles indicate the data for concomitant antibiotic use for a contemplated acetaminophen composition and the Tylenol® Immediate Release Elixir product, respectively, and the empty circles and triangles indicate the data for no antibiotic use for a contemplated acetaminophen composition and the Tylenol® Immediate Release Elixir product, respectively, it is readily apparent that use of a contemplated acetaminophen composition, with or without concomitant antibiotic use, exhibited increased and prolonged fever reduction compared to an equivalent amount of the Tylenol® Immediate Release Elixir product. This result was also unexpected.

Surprisingly, in viewing the concomitant antibiotic data of the Tylenol® Immediate Release Elixir product, compared to a contemplated acetaminophen composition, a contemplated composition exhibited an increase in fever reduction with the concomitant antibiotic use, whereas the Tylenol® Immediate Release Elixir product showed a lesser effect when used with antibiotics. For example, referring to FIG. 2, at 3 hours post initial administration, a contemplated acetaminophen composition when used with antibiotics exhibited a mean temperature reduction of about 2.4° F. (from about 102.5° F. to about 100.1° F.), whereas the Tylenol® Immediate Release Elixir product exhibited a temperature reduction of only about 2.1° F. (from about 102.7° F. to about 100.6° F.)

This difference is more dramatic at four hours after administration (at the time of the second Tylenol® Immediate Release Elixir product administration), where it can be seen that the effectiveness of the Tylenol® Immediate Release Elixir decreased, whereas the effectiveness of a contemplated acetaminophen composition increased, and the mean temperature reduction differences were about 2.5° F. (from about 102.5° F. to about 100.0° F.) for a contemplated acetaminophen composition and about 1.9° F. (from about 102.7° F. to about 100.8° F.) for the Tylenol® Immediate Release Elixir product. It is interesting to note that at all times during the study, with respect to concomitant antibiotic use, the mean temperature data for a contemplated acetaminophen composition was lower than that for the Tylenol® Immediate Release Elixir product.

The data that are illustrated in FIG. 3 are segregated by high and low baseline temperatures for a contemplated acetaminophen composition and the Tylenol® Immediate Release Elixir product (illustrated as filled circles for a contemplated acetaminophen composition and filled triangles for the Tylenol® Immediate Release Elixir product, at high baseline temperatures and as empty circles for a contemplated acetaminophen composition and empty triangles for the Tylenol® Immediate Release Elixir product, at low baseline temperatures).

As can be seen from the data, a contemplated acetaminophen composition exhibited a significantly greater temperature reduction in children with high baseline temperatures at both three and four hours after administration, of about 3.2° F. (from about 104° F. to about 100.8° F.) compared to the Tylenol® Immediate Release Elixir product, which exhibited a temperature decrease of only about 2.6° F. and 2.2° F., respectively at three and four hours (from about 103.8° F. to about 101.2° F. at three hours, which subsequently increased to about 101.6° F. at four hours). Thus, a contemplated acetaminophen composition exhibited considerable effectiveness in achieving high baseline temperature reductions compared to the Tylenol® Immediate Release Elixir product. Again, this was an unexpected result.

At lower baseline temperatures, a contemplated acetaminophen preparation exhibited greater temperature reduction, with a greatest difference at four hours, where the present acetaminophen preparation exhibited a temperature reduction of about 2.1° F. (from about 102.0° F. to about 99.9° F.) compared to the Tylenol® Immediate Release Elixir product, which showed a temperature reduction of about 1.6° F. (from about 101.9° F. to about 100.3° F.).

The results of the in vivo study data were statistically assessed using Fisher's Exact Test for categorical data and using Wilcoxon Rank Sum Test for continuous variables. Efficacy end points were compared using the Wilcoxon Rank Sum Test and a linear regression model was used to assess the treatment effect adjusted for potential confounders.

Statistically significant differences in mean temperatures between a contemplated acetaminophen composition (single dose) and the Tylenol® Immediate Release Elixir product (two doses) were shown at four and five hours after initial administration that favored a contemplated acetaminophen composition. There was generally a greater magnitude of temperature reduction in patients administered a contemplated acetaminophen composition than those administered the Tylenol® Immediate Release Elixir product with high baseline temperatures than in those with low baseline temperatures. However, the patterns of temperature reduction in patients with high and low baseline temperatures were similar to each other and similar to the patterns seen in the overall analysis.

The mean area-under-curve (AUC) values from initial administration to four hours post administration for all patients; i.e., overall results, were generally greater for a contemplated acetaminophen composition than those for the Tylenol® Immediate Release Elixir product.

As provided herein, the present extended release acetaminophen composition provides long term, extended relief in a palatable form. A contemplated acetaminophen composition permits administering the medication to a child so that the child can benefit from an extended release formulation. This can be extremely beneficial at night, so that a child can rest or sleep comfortably for a sufficiently long period of time, eight or more hours, while under the effects of the analgesic if the child is in pain, or under the effects of the antipyretic if the child is febrile. Parents know all too well that a "good night's rest" can be beneficial to the comfort and recovery of an ill child.

Another trial study was conducted to determine the efficacy of a contemplated acetaminophen composition compared to a known analgesic (Tylenol® Extended Relief caplets), and a placebo, over an eight hour period, for the relief of pain from oral surgery, specifically, the surgical removal of impacted third molars. In this study, 125 patients were randomly administered 1300 mg of a contemplated acetaminophen composition, 1300 mg of Tylenol® Extended Relief Caplets or a placebo.

The results of this study indicate that patients to whom the contemplated acetaminophen composition and the Tylenol® Extended Relief Caplet product were administered, experienced mean pain intensity difference scores that were significantly higher than those patients to whom the placebo were administered. No significant pair-wise differences were exhibited between the contemplated acetaminophen composition and the Tylenol® Extended Relief Caplet product.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An extended release acetaminophen composition comprising particles containing acetaminophen coated on sugar/starch seeds, said particles being present as a blend of both an immediate release and a controlled release form and also coated sugar/starch seeds that are free of acetaminophen, wherein said immediate release particles, said controlled release particles and said coated sugar/starch seeds are present in said blend at a weight ratio of about 1:1–1.5:0.1–0.25, said composition when contained within a gelatin capsule and assayed in a USP Apparatus I rotating basket at 50 rpm in 900 mL of phosphate buffer at pH 5.8 and 37° C. exhibiting about 40 percent acetaminophen dissolution at one-half hour, about 55 percent acetaminophen dissolution at one hour, and substantially complete dissolution of acetaminophen at six hours.

2. An extended release acetaminophen composition comprising:

discrete particles of sugar/starch seeds coated with a plurality of layers of acetaminophen and magnesium stearate that are bound with povidone forming controlled release particles;

discrete particles of sugar/starch seed coated with a plurality of layers of a mixture of acetaminophen, starch and cross-linked carboxymethyl cellulose that are bound with povidone forming immediate release particles; and discrete particles of coated sugar/starch seeds that are free of acetaminophen;

wherein said controlled release particles, said immediate release particles and said coated sugar/starch seeds are present as a blend in which said immediate release particles, said controlled release particles and said coated sugar/starch seeds are present in said blend at a weight ratio of about 1:1–1.5:0.1–0.25, and wherein said blend, when assayed in a USP Apparatus I rotating basket at 50 rpm in 900 mL of phosphate buffer at pH 5.8 and 37° C. exhibits about 40 percent acetaminophen dissolution at one-half hour, about 55 percent acetaminophen dissolution at one hour, and substantially complete dissolution of acetaminophen at six hours.

* * * * *